United States Patent
Tam et al.

(10) Patent No.: US 7,893,269 B2
(45) Date of Patent: Feb. 22, 2011

(54) PROCESS FOR THE MANUFACTURE OF 3-HYDROXY-N-ALKYL-1-CYCLOALKY1-6-ALKYL-4-OXO-1,4-DIHYDROPYRIDINE-2-CARBOXAMIDE AND ITS RELATED ANALOGUES

(75) Inventors: Tim Fat Tam, Woodbridge (CA); Regis Leung-Toung, Mississauga (CA); Yanqing Zhao, Toronto (CA); Wanren Li, Toronto (CA); Yingsheng Wang, Toronto (CA); Sandra Vittoria Agostino, Toronto (CA); Birenkumar Hasmukhbhai Shah, Toronto (CA)

(73) Assignee: Apotex Inc, Toronto (CA)

( * ) Notice: Subject to any disclaimer, the term of this patent is extended or adjusted under 35 U.S.C. 154(b) by 931 days.

(21) Appl. No.: 11/667,751

(22) PCT Filed: Nov. 17, 2005

(86) PCT No.: PCT/CA2005/001746

§ 371 (c)(1),
(2), (4) Date: May 15, 2007

(87) PCT Pub. No.: WO2006/053429

PCT Pub. Date: May 26, 2006

(65) Prior Publication Data

US 2008/0096886 A1    Apr. 24, 2008

(30) Foreign Application Priority Data

Nov. 19, 2004   (CA) .................................... 2488034

(51) Int. Cl.
*C07D 403/02*    (2006.01)
(52) U.S. Cl. ........................ 546/298; 544/128; 544/360; 546/276.4
(58) Field of Classification Search ........................ None
See application file for complete search history.

(56) References Cited

U.S. PATENT DOCUMENTS

| | | | |
|---|---|---|---|
| 4,840,958 A | 6/1989 | Hider et al. |
| 4,975,538 A | 12/1990 | Barbachyn et al. |
| 5,480,894 A | 1/1996 | Hider et al. |
| 5,688,815 A | 11/1997 | Zbinden |
| 6,335,353 B1 | 1/2002 | Hider et al. |
| 6,426,418 B1 | 7/2002 | Tam et al. |
| 6,465,229 B2 | 10/2002 | Cahoon et al. |
| 6,472,532 B1 | 10/2002 | Tam et al. |
| 6,476,229 B1 | 11/2002 | Tam et al. |

FOREIGN PATENT DOCUMENTS

| | | |
|---|---|---|
| CA | 2379370 | 9/2003 |
| NZ | 529657 | 7/2004 |
| WO | WO 2005049609 | 6/2005 |

OTHER PUBLICATIONS

Piyamongkol et al, Tetrahedron, 57 (2001), pp. 3479-3486.*
International Search Report of PCT/CA05/01746, Apr. 2005.*
Dimethylchloromethyleneammonium Chloride. In: Encyclopedia of Reagents in Organic Synthesis, vol. 3, Leo A. Paquette (Ed.), John Wiley & Sons, Chichester, 1995, pp. 2045-2047.
Oxalyl Chloride-Dimethylformamide. In: Encyclopedia of Reagents in Organic Synthesis, vol. 6, Leo A. Paquette (Ed.), John Wiley & Sons, Chichester, 1995, pp. 3818-3820.
Liu, Z.D., et al., (1999), J. Med. Chem., 42(23), pp. 4814-4823.
Protective Groups. In: Protective Groups in Organic Synthesis, Theodora W. Greene & Peter G. M. Wuts (Eds.), 3rd Edition, John Wiley & Sons Inc., New York, 1999, pp. xiii-xvi.
Liu, Z.D., et al., (2001), Bioorganic & Medicinal Chemistry, 9, pp. 563-573.
Tam, T.F., et al., (2003), Current Medicinal Chemistry, 10, pp. 983-995.
Liu, et al., Biochemical Pharmacology, vol. 61, issue 3, pp. 285-290 (2001).
Liu, et al., J. Chromatogarphy B., vol. 730, issue 1, pp. 135-139 (1999).
Merkofer, et al., Helvetica Chim. Acta., vol. 87, pp. 3021-3034 (2004).

* cited by examiner

*Primary Examiner* — Zinna N Davis

(57) ABSTRACT

The present invention relates to a novel process for the preparation of 1-alkyl or 1-cycloalkyl derivatives of 3-hydroxy-4-oxo-1,4-dihydropyridine-2-carboxamide of formula (I). The process includes reacting an amine $R^2NH_2$ with a compound of formula (II) in a solution of metal hydroxide in water to give a compound of formula (III). Subsequent reaction of the compound of formula (III) with an acid chloride formation reagent in an inert solvent gives compounds of formula (I). The acid chloride formation reagent is selected from oxalyl chloride and dimethylformamide, dimethylchloromethyleneammonium chloride and thionyl chloride and dimethylformamide. If desired, a compound of formula (I) where $R^5$ is hydrogen may be formed when an intermediate substituent is used wherein $R^5$ is an alcohol protective group removable by catalytic hydrogenation.

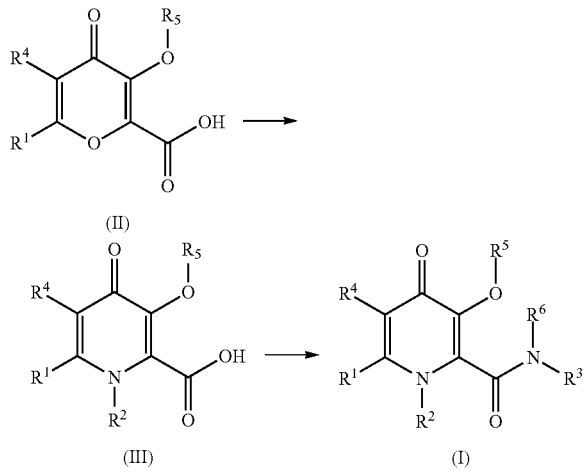

22 Claims, No Drawings

PROCESS FOR THE MANUFACTURE OF 3-HYDROXY-N-ALKYL-1-CYCLOALKY1-6-ALKYL-4-OXO-1,4-DIHYDROPYRIDINE-2-CARBOXAMIDE AND ITS RELATED ANALOGUES

This is a national stage entry of PCT international application PCT/CA2005/001746, filed on Nov. 17, 2005 and claims foreign priority to Canadian patent application 2,488,034, filed on Nov. 19, 2004, now issued as Canadian Patent 2,488,034 on Oct. 6, 2009.

FIELD OF THE INVENTION

This invention relates to a process for the manufacture of a 3-hydroxy derivative of 4-oxo-1,4-dihydropyridine-2-carboxamide and for the manufacture of intermediates useful in the manufacturing of a 3-hydroxy derivative of 4-oxo-1,4-dihydropyridine-2-carboxamide.

BACKGROUND OF THE INVENTION

Members of the 3-hydroxy-4-oxo-1,4-dihydropyridine class are well known for their ability to chelate iron in physiological environments and have been reported to be useful in treating iron related disorders such as thalassaemia and anemia (see U.S. Pat. Nos. 4,840,958; 5,480,894; 5,688,815; Liu et. al, J. Med. Chem. 1999, 42(23), 4814-4823).

Derivatives of 3-hydroxy-4-oxo-1,4-dihydropyridine-2-carboxamide (formula I) are bidentate iron chelators with potential for oral administration (Bioorganic & Medicinal Chemistry 2001, 9, 563-567; Current Medicinal Chemistry 2003, 10, 983-995; U.S. Pat. No. 6,335,353 and NZ 529657). Selected compounds of formula I have been orally tested using an iron mobilization efficacy assay in the rat (see Table 3 of U.S. Pat. No. 6,335,353 and example 12 of NZ 529657). Such compounds of formula I are chelators possessing high $pFe^{3+}$ values and hence show great promise in their ability to remove iron under in-vivo conditions.

There are several reported syntheses of 3-hydroxy-N,1-disubstituted-6-methyl-4-oxo-1,4-dihydropyridine-2-carboxamides. The starting material for the synthesis of the acid (1) is reported in U.S. Pat. No. 6,472,532 and shown in scheme 1:

Scheme 1:

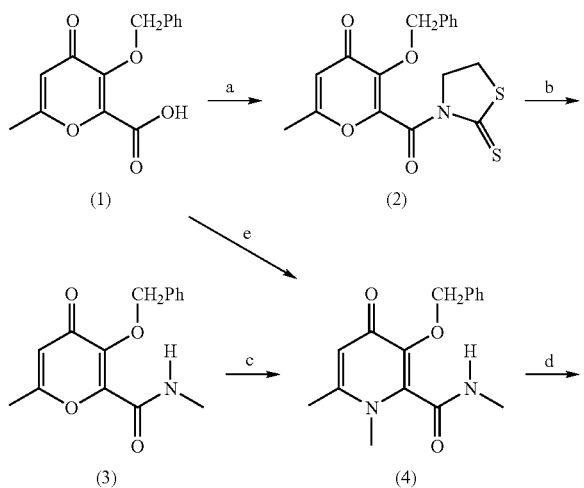

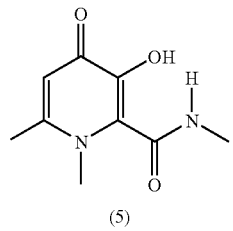

Scheme 1: a. DCC, $CH_2Cl_2$, 2-mercaptothiazoline;
b. $MeNH_2$, THF;
c. $MeNH_2$, MeOH;
d. $H_2$, Pd/C, EtOH;
e. 1,1'-carbonyldiimadazole, DMF, $CH_3NH_2$.

In the first approach described in U.S. Pat. No. 6,335,353, a representative compound, 3-hydroxy-N,1,6-trimethyl-4-oxo-1,4-dihydropyridine-2-carboxamide (CP502; (5)) has been prepared by the method described in examples 45 to 48, 53 and 58 of U.S. Pat. No. 6,335,353. The 2-carboxyl derivative (1) is prepared from allomaltol in three steps. The derivative (1) reacts with dicyclohexyl-carbodiimide (DCC), 2-mercaptothiazoline and 4-dimethylaminopyridine to give 3-(2-carbonyl-3-benzyloxy-6-methyl-4(1H)-pyran-2-yl)-1,3-thiazolidine-2-thione (2) which is subsequently reacted with methylamine ($MeNH_2$) in tetrahydrofuran (THF) to give 3-benzyloxy-6-methyl-4(1H)-pyran-2-yl)-2-carboxy-(N-methyl)-amide (3). The 3-benzyloxy-6-methyl-4(1H)-pyran-2-yl)-2-carboxy-(N-methyl)-amide (3) is converted to 1,6-dimethyl-3-benzyloxy-4(1H)-pyridinone-2-carboxy-(N-methyl)-amide (4) with methylamine in alcohol, in particular methanol (MeOH). The 3-benzyloxy derivative (4) was deprotected with hydrogenation using Pd/C in ethanol as illustrated in Scheme 1 to give CP502 (5).

In a second approach reported in US 6,476,229, compound (1) is reacted with 1,1'-carbonyl diimidazole (1,1'-CDI) and methylamine to give the compound (4) directly (step e of scheme 1). This approach reduces the two step conversion of (1) to (4) into a single process step. The 3-benzyloxy derivative (5) was deprotected with hydrogenation using Pd/C in ethanol as illustrated in Scheme 1 to give CP502 (5).

In a third approach described in NZ 529657, the method in step e of scheme 1 was modified to prepare 1-cyclopropyl-3-hydroxy-6-methyl-4-oxo-1,4-dihydro-pyridine-2-carboxylic acid methylamide (Apo6619) (see scheme 2 below). Acid (1) was reacted with 1,1'-carbonyldiimidazole to give the amide (3). Subsequent reaction of (3) with cyclopropylamine in alcohol affords compound (6) in moderate yield. The 3-benzyloxy derivative (6) was deprotected with hydrogenation using Pd/C in ethanol or methanol to give compound Apo6619.

Scheme 2:

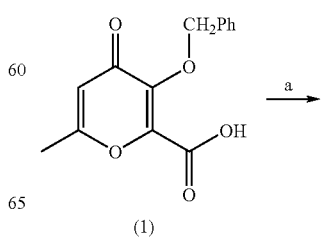

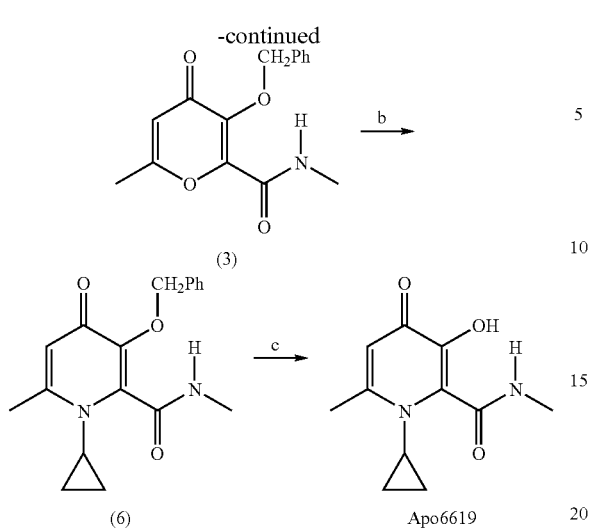

Scheme 2: a. 1,1'-carbonyldiimidazole, DMF, CH₃NH₂;
b. c-PrNH₂, MeOH, reflux;
c. H₂, Pd/C, MeOH or EtOH.

In general, all three approaches share the amide intermediate (3A) (Scheme 3). Insertion of either an alkylamine or cycloalkylamine R'NH₂ (R'=alkyl or cycloalkyl) into the 3-benzyloxy-6-methyl-4-oxo-4H-pyran-2-carboxylic acid methylamide affords the 3-hydroxy-4-pyridinone (5A). However, such insertion reaction proceeds in less than 60% yield and generates by-products when the R'NH₂ is a hindered alkylamine or cycloalkylamine, creating problematic isolation of the product by crystallization at the manufacturing scale.

Scheme 3:

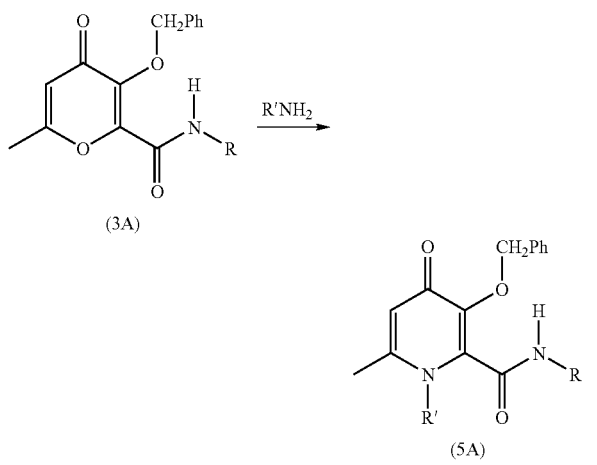

Whilst there exists a number of reaction routes for the formation of 4-oxo-1,4-dihydropyridine-2-carboxamides analogues and derivatives thereof, known processes do not provide sufficient yield for industrial application and further, result in the need of toxic and/or hazardous waste disposal.

It is therefore an object of the present invention to provide an improved process for the production of 1-cyclopropyl-3-hydroxy-N,6-dimethyl-4-oxo-1,4-dihydropyridine-2-carboxamide and 3-(benzyloxy)-1-cyclopropyl-N,6-dimethyl-4-oxo-1,4-dihydropyridine-2-carboxamide from 3-(benzyloxy)-1-cyclopropyl-6-methyl-4-oxo-1,4-dihydropyridine-2-carboxylic acid, which can be prepared at yields sufficiently high for industrial application.

SUMMARY OF THE INVENTION

In particular aspects, the present invention provides a process for the manufacture of a 3-hydroxy derivative of 4-oxo-1,4-dihydropyridine-2-carboxamide of formula I

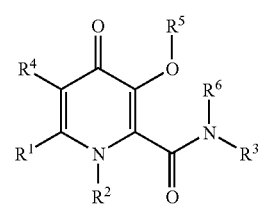

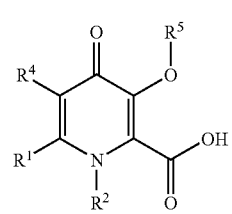

wherein:
R¹ is selected from the group consisting of hydrogen and $C_1$-$C_6$ alkyl;
R² is selected from the group consisting of $C_1$-$C_6$ alkyl and $C_3$-$C_6$ cycloalkyl;
R³ is selected from the group consisting of $C_1$-$C_6$ alkyl, $C_3$-$C_6$ cycloalkyl, hydrogen and $C_1$-$C_6$ alkyl-[$C_3$-$C_6$ cycloalkyl] with the attachment at the alkyl group;
R⁴ is selected from the group consisting of hydrogen and $C_1$-$C_6$ alkyl;
R⁵ is selected from the group consisting of hydrogen, benzyl and a benzyl group substituted with 1 to 3 substituents selected from halo, $C_1$-$C_4$ alkyl and $C_1$-$C_4$ alkoxy or any alcohol protective group removable using acid/base hydrolysis or catalytic hydrogenation;
R⁶ is selected from the group consisting of $C_1$-$C_6$ alkyl, $C_3$-$C_6$ cycloalkyl and hydrogen;
or
R³R⁶N when taken together, form a heterocyclic ring selected from piperidinyl, morpholinyl, pyrrolidinyl or piperazinyl, wherein the group piperidinyl, morpholinyl, pyrrolidinyl or piperazinyl is either unsubstituted or substituted with one to three $C_1$-$C_6$ alkyl groups;
wherein the process for the manufacture of the compound of formula I includes the steps of:
(i) reacting a compound of formula III wherein R¹, R², R⁴, and R⁵ are as defined above with one or more acid chloride formation reagents; and
(ii) reacting an amine R³R⁶NH wherein R³ and R⁶ are as defined above to give a compound of formula I, provided that, when R⁵ is hydrogen, the R⁵ substituent is an alcohol protective group removable by acid/base hydrolysis or catalytic hydrogenation.

In another aspect, the invention resides in a process for the manufacture of a compound of formula III as herein before described, including the step of:

reacting an amine $R^2NH_2$ wherein $R^2$ is selected from the group consisting of $C_1$-$C_6$ alkyl and $C_3$-$C_6$ cycloalkyl with a compound of formula II

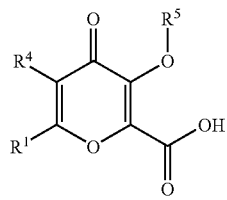

II wherein $R^1$, $R^4$, and $R^5$ are as defined above, in an aqueous solution of metal hydroxide wherein the metal is sodium or potassium to give a compound of formula III as herein before described wherein $R^1$, $R^2$, $R^4$ and $R^5$ are as defined above.

In yet another aspect, the invention resides in a process for the manufacture of a compound of formula IA

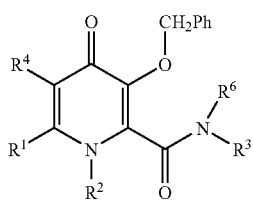

IA including the step of reacting a compound of formula III wherein $R^1$, $R^2$, $R^4$, and $R^5$ are as defined above with one or more acid chloride formation reagents.

It will be appreciated that the protective group $R^5$ in formulae I, II, III and IA is not limited to benzyl and benzyl substituted with 1 to 3 substituents as described above and that any known alcohol protective groups which can be removed by catalytic hydrogenation or acid/base hydrolysis are contemplated. For example, known alcohol protective groups can be selected from the following non-limiting examples, benzyl, 2,6-dimethylbenzyl, 4-methoxybenzyl, o-nitrobenzyl, 2,6-dichlorobenzyl, 3,4-dichlorobenzyl, 4-(dimethylamino)carbonylbenzyl, 4-methylsulfinylbenzyl, 9-anthrylmethyl, 4-picolyl, heptafluoro-p-tolyl, tetrafluoro-4-pyridyl, formate, acetate, benzoate, benzyloxycarbonyl, methoxycarbonyl, t-butyloxycarbonyl, 2,2,2-trichloroethoxycarbonyl, methoxymethyl, benzyloxymethyl, methoxyethoxymethyl, t-butyl (eg. "Protective Groups in Organic Synthesis, Third ed., Theodora W. Greene & Peter G. M. Wuts, John Wiley & Sons Inc. 1999" reports an extensive list of alcohol protective groups for functional alcohols and phenol groups).

Accordingly, the present invention provides a process for the preparation of 3-(benzyloxy)-1-cyclopropyl-6-methyl-4-oxo-1,4-dihydropyridine-2-carboxylic acid;

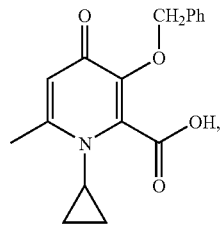

1-cyclopropyl-3-hydroxy-N,6-dimethyl-4-oxo-1,4-dihydropyridine-2-carboxamide;

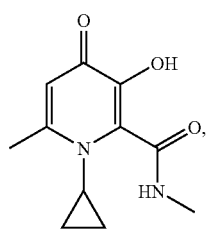

3-(benzyloxy)-1-cyclopropyl-N,6-dimethyl-4-oxo-1,4-dihydropyridine-2-carboxamide;

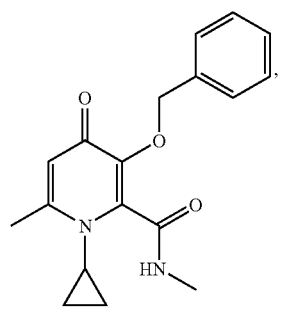

1-cyclopropyl-3-hydroxy-6-methyl-2-(morpholin-4-ylcarbonyl)pyridin-4(1H)-one;

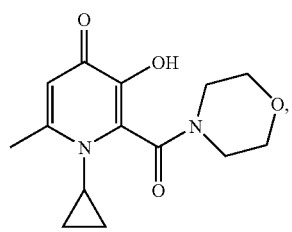

N-(cyclohexyl methyl)-1-cyclopropyl-3-hydroxy-6-methyl-4-oxo-1,4-dihydropyridine-2-carboxamide;

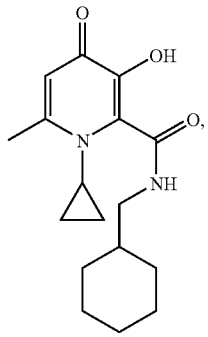

1-cyclopropyl-3-hydroxy-6-methyl-N-(3-methylbutyl)-4-oxo-1,4-dihydropyridine-2-carboxamide;

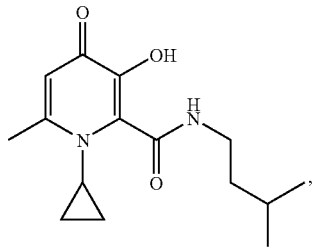

1-cyclopropyl-N-hexyl-3-hydroxy-6-methyl-4-oxo-1,4-dihydropyridine-2-carboxamide;

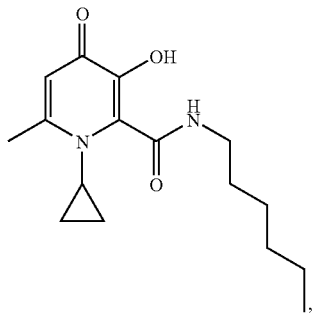

N-cyclohexyl-1-cyclopropyl-3-hydroxy-6-methyl-4-oxo-1,4-dihydropyridine-2-carboxamide;

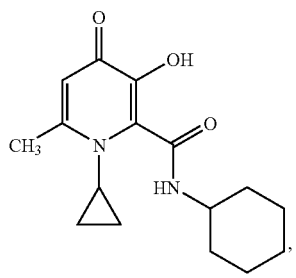

1-cyclopropyl-3-hydroxy-N,N,6-trimethyl-4-oxo-1,4-dihydropyridine-2-carboxamide;

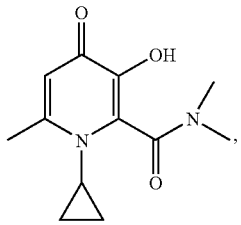

1-cyclopropyl-3-hydroxy-6-methyl-2-[(4-methylpiperazin-1-yl)carbonyl]pyridin-4(1H)-one; and

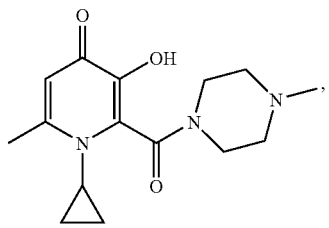

N,1-dicyclopropyl-3-hydroxy-6-methyl-4-oxo-1,4-dihydropyridine-2-carboxamide;

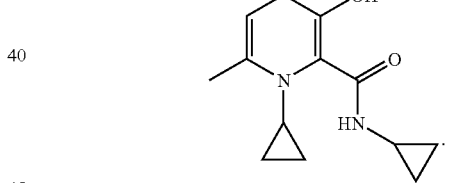

The invention resides in a process whereby reacting an acid of formula III with an acid chloride formation reagent results in the in situ formation of an intermediate acid chloride of the formula IV. Suitable acid chloride formation reagents include, but are not limited to, oxalyl chloride and dimethylformamide (Encyclopedia of Reagents in Organic Synthesis, Leo A. Paquette, vol. 6, p. 3818-3820, John Wiley & Sons, 1995), Vilsmeier's reagent (dimethylchloromethylene-ammonium chloride) and thionyl chloride with dimethylformamide in an inert solvent to give the intermediate acid chloride of formula IV in situ. Also contemplated are the chemical equivalents of the Vilsmeier's reagent, i.e. the combined use of phosphorus oxychloride with dimethylformamide, phosgene with dimethylformamide, and thionyl chloride combined with dimethylformamide (Encyclopedia of Reagents in Organic Synthesis, Leo A. Paquette, vol. 3, p. 2045-2047, John Wiley & Sons, 1995). The acid chloride intermediate IV is reacted with an amine of $R^3R^6NH$ to give a compound of formula I.

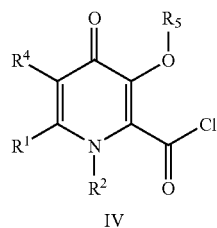

IV

Scheme 4:

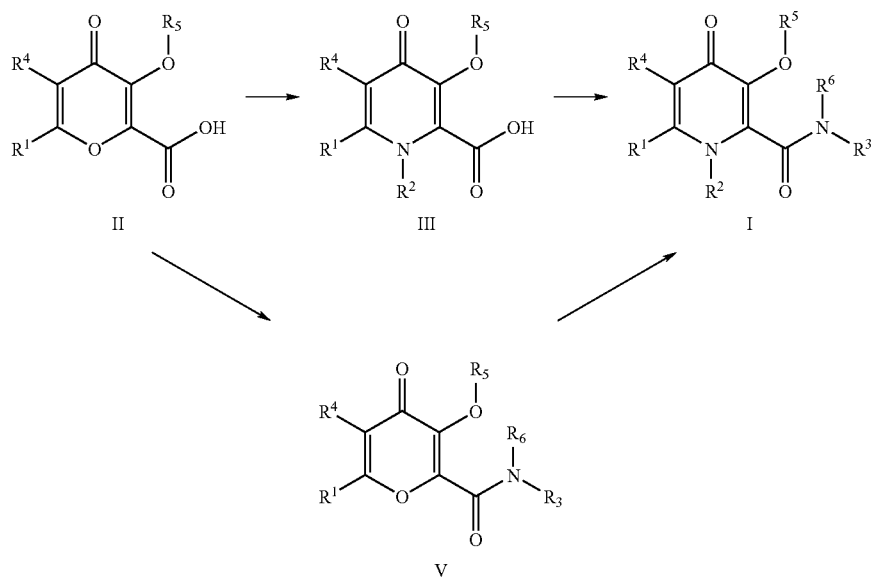

According to the novel process, compounds of formula I, which include the insertion of an amine $R^2NH_2$ (in aqueous metal hydroxide such as aqueous sodium hydroxide) in a compound of formula II via the compound of formula III are synthesized (scheme 4). This novel process offers significant advantages over the process using $R^2NH_2$ in methanol as described in CA 2379370.

Advantageously, when the process is carried out in the presence of aqueous sodium hydroxide solution, the amount of $R^2NH_2$ required is reduced and methanol is no longer used as a solvent. Thus the process is both cost effective and removes the costly aspect of toxic methanol waste disposal.

Compound III is subsequently reacted with an acid chloride forming reagent, eg. oxalyl chloride and dimethylformamide, Vilsmeier reagent or thionyl chloride and dimethylformamide, in an inert solvent, followed by the quenching with an amine $R^3R^6NH$ to give the amide of formula I in a single process step. If desired, the alcohol protective group can be removed to give a compound of formula I wherein $R^5$ is hydrogen. It will be appreciated that this synthetic process (in converting compounds of formula II to III to 1) is surprisingly superior to known syntheses of compounds of formula I using compound V as the key intermediate as it affords both high reaction yields and high purity over known processes.

As used herein:

"$C_1$-$C_6$ alkyl" means a branched or unbranched saturated hydrocarbon chain having, unless otherwise noted, one to six carbon atoms, including but not limited to methyl, ethyl, propyl, isopropyl, n-propyl, butyl, sec-butyl, isobutyl, n-pentyl, hexyl, octyl and the like.

"$C_3$-$C_6$ cycloalkyl" refers to a cyclic hydrocarbon radical consisting solely of carbon and hydrogen, containing no unsaturation and having from three to eight carbon atoms, e.g. cyclopropyl, cyclobutyl, cyclopentyl, cyclohexyl.

"$C_1$-$C_6$ Alkoxy" refers to a radical of the formula —O—[$C_1$-$C_6$ alkyl] wherein $C_1$-$C_6$ alkyl as defined above, e.g., methoxy, ethoxy, n-propoxy, 1-methylethoxy, n-butoxy, t-butoxy.

"$C_1$-$C_6$ alkyl-[$C_3$-$C_6$ cycloalkyl] with the attachment at the alkyl group" refers to a hydrocarbon radical consisting solely of hydrogen and carbon, containing no unsaturation and having three to six carbon atoms in the cycloalkyl part and one to six carbon atom in the alkyl portion. The attachment point is the $C_1$-$C_6$ alkyl-[$C_3$-$C_6$ cycloalkyl] substituent is at the alkyl chain. Examples are cyclohexylmethyl, 2-cyclopropylethyl, 2-cyclobutylethyl cyclopentylmethyl, etc.

"phenyl-($C_1$-$C_6$)-alkyl with the attachment point at the alkyl group" refers to a phenylalkyl group wherein the alkyl chain consists of $C_1$-$C_6$ carbon atoms. The substituent is attached at the alkyl portion of the phenylalkyl chain. Examples are benzyl, 2-phenylethyl, 3-phenylpropyl, 2-phenylbutyl, etc.

In illustrative embodiments of the present invention, there is provided a process for the manufacture of a compound of formula I

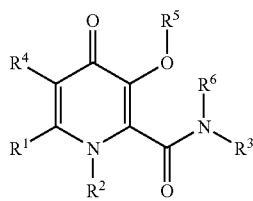

comprising: reacting one or more acid chloride formation reagents with a compound of formula III

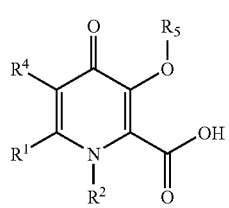

thereby forming an intermediate; and reacting the intermediate with an amine $R^3R^6NH$ to give a compound of formula I, wherein: $R^1$ is selected from the group consisting of hydrogen and $C_1$-$C_6$ alkyl; $R^2$ is selected from the group consisting of $C_1$-$C_6$ alkyl and $C_3$-$C_6$ cycloalkyl; $R^3$ is selected from the group consisting of $C_1$-$C_6$ alkyl, $C_3$-$C_6$ cycloalkyl, hydrogen and $C_1$-$C_6$ alkyl-[$C_3$-$C_6$ cycloalkyl] with the attachment at the alkyl group; $R^4$ is selected from the group consisting of hydrogen and $C_1$-$C_6$ alkyl; $R^5$ is selected from the group consisting of hydrogen, benzyl, a substituted benzyl, and an alcohol protective group removable using acid/base hydrolysis or catalytic hydrogenation, wherein the substituted benzyl is substituted with 1 to 3 substituents selected from the group consisting of halo, $C_1$-$C_4$ alkyl and $C_1$-$C_4$ alkoxy ; $R^6$ is selected from the group consisting of $C_1$-$C_6$ alkyl, $C_3$-$C_6$ cycloalkyl and hydrogen; or $R^3R^6N$ when taken together form an unsubstituted or substituted heterocyclic ring selected from the group consisting of piperidinyl, morpholinyl, pyrrolidinyl and piperazinyl, wherein the substituted heterocyclic ring is substituted with one to three $C_1$-$C_6$ alkyl groups; $R^7$ is selected from the group consisting of benzyl, a substituted benzyl, and an alcohol protective group removable using acid/base hydrolysis or catalytic hydrogenation, wherein the substituted benzyl is substituted with 1 to 3 substituents selected from the group consisting of halo, $C_1$-$C_4$ alkyl and $C_1$-$C_4$ alkoxy; and provided that, when $R^5$ is hydrogen, $R^7$ is an alcohol protective group removable by acid/base hydrolysis or catalytic hydrogenation and $R^7$ is removed by acid/base hydrolysis or catalytic hydrogenation after reacting the intermediate with the amine.

In illustrative embodiments of the present invention, there is provided a process for the manufacture of a compound of formula I

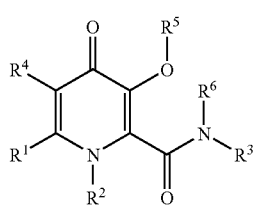

the process comprising:

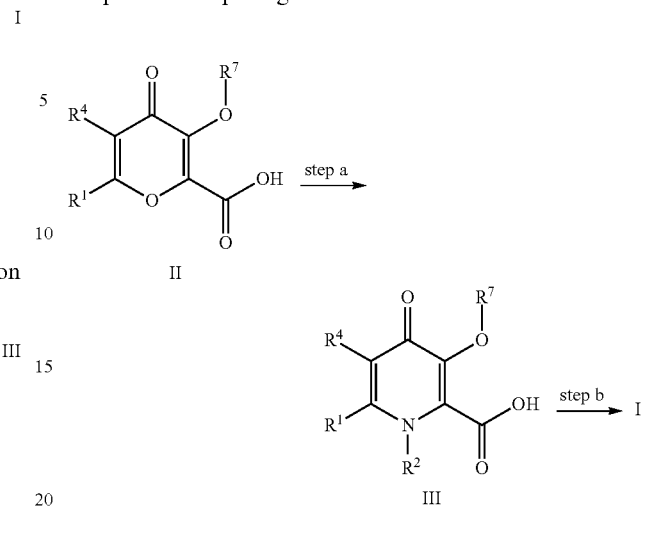

wherein step a comprises: reacting a first amine $R^2NH_2$ with a compound of formula II in an aqueous solution selected from the group consisting of aqueous sodium hydroxide solution, aqueous potassium hydroxide solution and mixtures thereof, to give a compound of formula III; and step b comprises: reacting the compound of formula III with an acid chloride formation reagent thereby forming an intermediate; and reacting the intermediate with a second amine $R^3R^6NH$, to give a compound of formula I, wherein: $R^1$ is selected from the group consisting of hydrogen and $C_1$-$C_6$ alkyl; $R^2$ is selected from the group consisting of $C_1$-$C_6$ alkyl and $C_3$-$C_6$ cycloalkyl; $R^3$ is selected from the group consisting of $C_1$-$C_6$ alkyl, $C_3$-$C_6$ cycloalkyl, hydrogen and $C_1$-$C_6$ alkyl-[$C_3$-$C_6$ cycloalkyl] with the attachment at the alkyl group; $R^4$ is selected from the group consisting of hydrogen and $C_1$-$C_6$ alkyl; $R^5$ is selected from the group consisting of hydrogen, benzyl, a substituted benzyl, and an alcohol protective group removable using acicVbase hydrolysis or catalytic hydrogenation, wherein the substituted benzyl is substituted with 1 to 3 substituents selected from the group consisting of halo, $C_1$-$C_4$ alkyl and $C_1$-$C_4$ alkoxy; $R^6$ is selected from the group consisting of $C_1$-$C_6$ alkyl, $C_3$-$C_6$ cycloalkyl and hydrogen; or $R^3R^6N$ when taken together, form an unsubstituted or substituted heterocyclic ring selected from the group consisting of piperidinyl, morpholinyl, pyrrolidinyl or piperazinyl, wherein the substituted heterocyclic ring is substituted with one to three $C_1$-$C_6$ alkyl; and $R^7$ is selected from the group consisting of benzyl, substituted benzyl, and an alcohol protective group removable using acidfbase hydrolysis or catalytic hydrogenation, wherein the substituted benzyl is substituted with 1 to 3 substituents selected from the group consisting of halo, $C_1$-$C_4$ alkyl and $C_1$-$C_4$ alkoxy; and provided that, when $R^5$ is hydrogen, $R^7$ is an alcohol protective group removable by acid/base hydrolysis or catalytic hydrogenation and $R^7$ is removed by acid/base hydrolysis or catalytic hydrogenation after reaction of the intermediate with the second amine.

In illustrative embodiments of the present invention, there is provided a process described herein wherein $R^5$ is benzyl and $R^7$ is benzyl.

In illustrative embodiments of the present invention, there is provided a process for the manufacture of a compound of formula IA

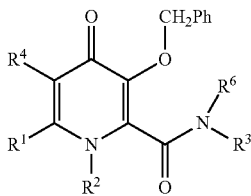

IA comprising: reacting one or more acid chloride formation reagents with a compound of formula

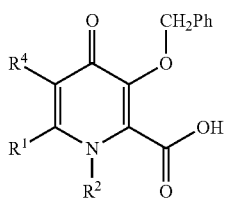

IIIA thereby forming an intermediate; and reacting the intermediate with an amine $R^3R^6NH$; wherein: $R^1$ is selected from the group consisting of hydrogen and $C_1$-$C_6$ alkyl; $R^2$ is selected from the group consisting of $C_1$-$C_6$ alkyl and $C_3$-$C_6$ cycloalkyl; $R^3$ is selected from the group consisting of $C_1$-$C_6$ alkyl, $C_3$-$C_6$ cycloalkyl, hydrogen and $C_1$-$C_6$ alkyl-[$C_3$-$C_6$ cycloalkyl] with the attachment at the alkyl group; $R^4$ is selected from the group consisting of hydrogen and $C_1$-$C_6$ alkyl; and $R^6$ is selected from the group consisting of $C_1$-$C_6$ alkyl, $C_3$-$C_6$ cycloalkyl and hydrogen; or $R^3R^6N$ when taken together form an unsubstituted or substituted heterocyclic ring selected from the group consisting of piperidinyl, morpholinyl, pyrrolidinyl and piperazinyl, wherein the substituted heterocyclic ring is substituted with one to three $C_1$-$C_6$ alkyl groups.

In illustrative embodiments of the present invention, there is provided a process described herein wherein the acid chloride formation reagent is selected from the group consisting of: oxalyl chloride and dimethylformamide; dimethylchloromethylene-ammonium chloride; and thionyl chloride and dimethylformamide.

In illustrative embodiments of the present invention, there is provided a process described herein wherein the acid chloride formation reagent is oxalyl chloride and dimethylformamide.

In illustrative embodiments of the present invention, there is provided a process described herein wherein the acid chloride formation reagent is dimethylchloromethylene-ammonium chloride.

In illustrative embodiments of the present invention, there is provided a process for the manufacture of a compound of formula III

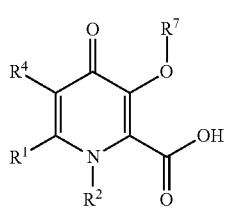

III comprising: reacting, in an aqueous solution of metal hydroxide selected from the group consisting of aqueous sodium hydroxide, aqueous potassium hydroxide and mixtures thereof, an amine $R^2NH_2$ with a compound of formula II

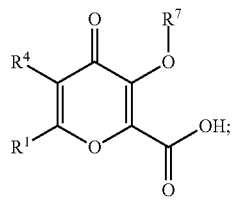

II wherein: $R^1$ is selected from the group consisting of hydrogen and $C_1$-$C_6$ alkyl; $R^2$ is selected from the group consisting of $C_1$-$C_6$ alkyl and $C_3$-$C_6$ cycloalkyl; $R^4$ is selected from the group consisting of hydrogen and $C_1$-$C_6$ alkyl; and $R^7$ is selected from the group consisting of benzyl, substituted benzyl, and an alcohol protective group removable using acid/base hydrolysis or catalytic hydrogenation, wherein the substituted benzyl is substituted with 1 to 3 substituents selected from the group consisting of halo, $C_1$-$C_4$ alkyl and $C_1$-$C_4$ alkoxy.

In illustrative embodiments of the present invention, there is provided a process described herein wherein $R^7$ is benzyl.

In illustrative embodiments of the present invention, there is provided a process described herein wherein $R^1$ is methyl.

In illustrative embodiments of the present invention, there is provided a process described herein wherein $R^2$ is cyclopropyl.

In illustrative embodiments of the present invention, there is provided a process described herein wherein $R^4$ is hydrogen.

In illustrative embodiments of the present invention, there is provided a process described herein wherein $R^3$ is methyl.

In illustrative embodiments of the present invention, there is provided a process described herein wherein $R^6$ is hydrogen.

DETAILED DESCRIPTION OF THE INVENTION

The synthesis of the acid of formula II ($R^4$=H, $R^1$=$CH_3$, $R^5$=$PhCH_2$—) is described in U.S. Pat. No. 6,426,418. This compound is converted into the amide of formula V by reacting with 1,1-carbonyl diimidazole and an amine $R^3R^6NH$ in an inert solvent (U.S. Pat. No. 6,426,418) in a single process step. However, insertion of a more hindered amine $R^2NH_2$ other than methylamine will only afford less than 50% yield of formula I and the end-product is contaminated with a number of unidentified by-products. Therefore the traditional approach reported above is unsuitable for large scale manufacturing of compounds of formula I wherein $R^2$ is $C_3$-$C_6$ cycloalkyl or a more hindered alkyl chain.

The present inventors have developed a new synthetic route for the compound of formula I which involves the conversion of the acid of formula II to the acid of formula III and subsequent reaction with an amine $R^2NH_2$ to give the amide of formula I.

The known synthesis of 3-(benzyloxy)-1,6-dimethyl-4-oxo-1,4-dihydropyridine-2-carboxylic acid, a compound of formula II is reported in example 1, CA 2379370. Compound II reacts with 3 to 8 equivalents of the amine $R^2NH_2$ in inert solvents at 60° C. to 110° C. to yield compound III. The preferred inert solvents for this reaction are methanol and ethanol. The use of other amines such as cyclopropylamine in methanol resulted in 3-(benzyloxy)-1-cyclopropyl-6-methyl- 4-oxo-1,4-dihydropyridine-2-carboxylic acid, however, and commercially significant, 4 to 6 fold excess of the amine was required.

The present inventors have surprisingly found that the above reaction occurs readily in water in the presence of substantially fewer molar equivalents (i.e. 2 to 3) of cyclopropylamine and 1 to 1.2 equivalents of sodium hydroxide. Commercially significant, methanol is no longer required as a solvent for the amine insertion reaction to form compound III from compound II.

Purification of compound III is carried out by simple recrystallization in the usual manner. As compound III is an intermediate, it must therefore meet the requirements for storage stability.

A compound of formula III is stable as a solid at room temperature. However, when compound III is thermally stressed by heating in a refluxing solvent above 100° C. for more than 4 hrs, decarboxylation of the acid of formula VI is observed. Hence, the new synthetic process to prepare the thermally stable compound III via amine insertion of compound II using aqueous sodium hydroxide rather than an organic solvent is highly unexpected. Significantly, the present isolation procedure and storage conditions are tailored for the intended long term use of compound III and results in high yields of compound III.

Traditional synthetic amide formation processes for the conversion of compound III to compound I were found unsuccessful, for example, where $R^5$=$PhCH_2$. The synthetic process for the conversion of compound III to compound I was found difficult as the preparation of the amide I from the acid of formula III ($R^5$=$PhCH_2$) was found problematic when using most traditional amide formation process. For example, the mixed anhydride process using isobutyl chloroformate, followed by the $R^2R^6NH$ in an inert solvent resulted in decarboxylation of the acid to give a compound of formula VI:

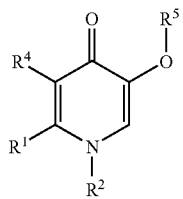

In another example, the use of 1,1'-carbonyldiimdazole (where $R^3R^6NH$) resulted in the decarboxylation of an acid of formula III to give a compound of formula VI. Similar results were obtained with dicyclohexyl-carbodiimide (where $R^3R^6NH$). A standard reagent used in the formation of an acid chloride of formula IV from an acid of formula III is thionyl chloride. When an acid of formula III is heated with thionyl chloride in an inert solvent such as toluene or methyl isobutyl ketone, the decarboxylated product of formula VI is the major product. Heating a mixture of an amine $R^3R^6NH$ with the acid of compound III does not result in the formation of compound I. Rather, decarboxylation of compound I to compound VI is observed.

The inventors have newly found that the conversion of the acid of formula III ($R^5$=$PhCH_2$) can be achieved by reacting a solution of the acid of formula III with an acid chloride formation reagent, eg. oxalyl chloride and dimethylformamide in an inert solvent to give the acid chloride of formula IV ($R^5$=$PhCH_2$) in situ. Quenching of the reaction mixture with the amine $R^2R^6NH$ affords the amide of formula I ($R^5$=$PhCH_2$). In addition, the compound of formula I can be easily isolated without the use of chromatography, instead, the pure material is obtained by simple recrystallization in high yields. It will be appreciated that other known acid chloride formation reagents can be used in the process. For example, the Vilsmeier reagent readily converts the acid of formula III ($R^5$=$PhCH_2$) to the compound of formula I. It is contemplated that thionyl chloride and dimethylformamide can also be used, however the product of formula I will be contaminated with sulfur and inorganic impurities and thus requires a further purification step.

In the following step, the alcohol protective group of a compound of formula I ($R^5$=$PhCH_2$) can be subsequently removed by catalytic hydrogenation with Pd/C as catalyst in alcohol. It will be appreciated however that hydrogenation can be equally achieved using Pd(OH)$_2$/C and raney Nickel.

Described above is the overall novel process for the conversion of compound II to III, to compound I in two simple steps. Following each step, the reaction product is isolated and purified by crystallization methods. In the case of formula I (wherein $R^5$=$PhCH_2$), the alcohol protective group can be removed by catalytic hydrogenation to give the compound of formula I ($R^5$=H).

The present invention will be more fully understood by the following examples, which illustrate the invention, but are not limited to the scope of the invention.

SPECIFIC DESCRIPTION OF THE MOST PREFERRED EMBODIMENTS

Example 1

Preparation of 3-benzyloxy-1-cyclopropyl-6-methyl-4-oxo-1,4-dihydro-pyridine-2-carboxylic acid Procedure I To a suspension of 3-(benzyloxy)-6-methyl-4-oxo-4H-pyran-2-carboxylic acid (70 g, 0.27 mol) in MeOH (350 mL) in a 3-necked RBF (round bottom flask) fitted with a mechanical stirrer was added cyclopropylamine (120 mL, 1.72 mol). A clear light yellow solution resulted. The reaction mixture was refluxed for ca. 19 h. Volatile solvents were removed in vacuo and the residue was dissolved in water (700 mL) with stirring. The aqueous mixture was filtered through a pad of Celite®. The filtrate was placed in a 3-necked RBF fitted with a mechanical stirrer, and cooled in an ice bath. Conc. HCl was added until the pH was ca. 1-2, and voluminous "orange" solid precipitated out. Acetone (200 mL) was added to the suspension. The solid was then collected by suction filtration, thoroughly washed with acetone, and air-dried. The title compound was obtained as an off-white solid (71.0 g, 88%). Mp: 139.0-139.5° C.; $^1$H-NMR (300 MHz, DMSO-D$_6$) δ(ppm): 0.98-1.15 (m, 4H, 2 c-CH$_2$), [2.37 (s)+2.40 (s), rotamers, 3/2 ratio, 3H, CH$_3$)], 3.30-3.50 (m, 1H, c-CH), 5.00-5.05 (m, 2H, CH$_2$Ph), 6.20-6.25 (m, 1H, C=CH), 7.28-7.50 (m, 5H, Ph); MS (m/z): 300.2 (M$^+$+1), 256.2, 192.2, 164.4, 91.0 (100%); Anal. Calcd. for C$_{17}$H$_{17}$NO$_4$: C, 68.21; H, 5.72; N, 4.68%. Found: C, 67.76; H, 5.76; N, 4.61%.

Procedure II:

To a suspension of 3-(benzyloxy)-6-methyl-4-oxo-4H-pyran-2-carboxylic acid (2.0 g, 7.685 mmol) in H$_2$O (10 ml) in a reaction tube with a stirrer was added a solution of 6N NaOH (1.33 ml, 8 mmol) at room temperature (RT). The resulting mixture was stirred at RT for 15 min until most of the starting material had dissolved. A light yellow solution was obtained upon addition of cyclopropylamine (1.60 ml, 23 mmol). The reaction mixture was then heated for ca. 20 h in the sealed tube. The reaction mixture was then poured into a flask containing 20 ml of $H_2O$. The mixture was acidified with a 10% HCl solution (ca. 5-6 ml) to pH=2 at RT. Precipitation occurred during the acidifying process. After stirring for 10 min, the solid was collected by suction filtration, thoroughly washed with $H_2O$ (2×5 ml), acetone (2×5 ml) and air-dried overnight. Thus, the title product (2.14 g, 93%) was obtained as an off-white solid.

Procedure III:

To a suspension of 3-(benzyloxy)-6-methyl-4-oxo-4H-pyran-2-carboxylic acid (2.0 g, 7.685 mmol) in $H_2O$ (10 ml) in a reaction tube with a stirrer, was added cyclopropylamine (2.13 ml, 30.74 mmol). A clear light yellow solution was formed. The reaction mixture was heated for ca. 19 h in a sealed tube. The reaction mixture then worked up as described in Procedure II. Thus, the title compound (2.14 g, 93%) was obtained as an off white solid.

Example 2

Preparation of 3-(benzyloxy)-1,6-dimethyl-4-oxo-1, 4-dihydropyridine-2-carboxylic acid methylamine salt As described previously, a 2 M methylamine solution in methanol (5.8 ml, 11.6 mmol) was added to a suspension of the 3-(benzyloxy)-6-methyl-4-oxo-4H-pyran-2-carboxylic acid (1.0 g, 3.84 mmol) in methanol (3 ml) at room temperature. The resulting solution was sealed, and then heated at 70° C. for overnight. A clear yellow solution was observed. The titled compound was obtained as a light yellow solid after solvent was removed by reducing pressure (1.02 g, 87% yield). $^1$H NMR (DMSO-$D_6$) δ(ppm): 7.8 (br, 2H), 7.49 (m, 2H), 7.3 (m, 3H), 6.03 (s, 1H), 4.91 (s, 2H), 3.47 (s, 3H), 2.35 (s, 3H), 2.24 (s, 3H); MS (m/z): 274 ($C_{15}H_{16}NO_4^+$).

The following compounds are prepared in a similar fashion:

3-Benzyloxy-1-ethyl-6-methyl-4-oxo-1,4-dihydropyridine-.2-carboxylic acid ethylamine salt $^1$H NMR (DMSO-$D_6$) δ(ppm): 7.90 (br, 2H), 7.48 (m, 2H), 7.30 (m, 3H), 6.00 (s, 1H), 4.91 (s, 2H), 3.92 (q, J=7.1 Hz, 2H), 2.80 (q, J=7.3 Hz, 2H), 2.27 (s, 3H), 1.29 (t, J=7.1 Hz, 3H), 1.12 (t, J=7.3 Hz, 3H); MS (m/z): 288 ($C_{16}H_{18}NO_4^+$).

3-Benzyloxy-6-methyl-4-oxo-1-propyl-1,4-dihydropyridine-2-carboxylic acid 1-propylamine salt.

$^1$H NMR (CDCl$_3$) δ(ppm): 8.0 (br, 2H), 7.47 (m, 2H), 7.25 (m, 3H), 6.39 (s, 1H), 5.07 (s, 2H), 3.92 (m, 2H), 2.58 (m, 2H), 2.28 (s, 3H), 1.85 (m, 2H), 1.51 (m, 2H), 0.95 (t, J=5.5 Hz, 3H), 0.79 (t, J=5.5 Hz, 3H); MS (m/z): 302 ($C_{17}H_{20}NO_4^+$).

Yield: 86%; 3-Benzyloxy-1-butyl-6-methyl-4-oxo-1,4-dihydropyridine-2-carboxylic acid 1-butylamine salt.

$^1$H NMR (DMSO-$D_6$) δ(ppm): 7.8 (br, 2H), 7.48 (m, 2H), 7.3 (m, 3H), 5.97 (s, 1H), 4.89 (s, 2H), 3.83 (m, 2H), 2.74 (m, 2H), 2.26 (s, 3H), 1.72 (m, 2H), 1.51 (m, 2H), 1.30 (m, 4H), 0.88 (m, 6H); MS (m/z): 316 ($C_{18}H_{22}NO_4^+$).

Yield: 84%; 1-Benzyl-3-benzyloxy-6-methyl-4-oxo-1,4-dihydropyridine-2-carboxylic acid benzylamine salt.

$^1$H NMR (DMSO-$D_6$) δ(ppm): 8.2 (br, 2H), 7.51 (m, 2H), 7.3 (m, 13H), 6.01 (s, 1H), 5.20 (s, 2H), 4.99 (s, 2H), 3.98 (s, 2H), 2.04 (s, 3H); MS (m/z): 350 ($C_{21}H_{20}NO_4^+$).

Yield: 86%; 3-Benzyloxy-6-methyl-4-oxo-1-(2-phenylethyl)-1,4-dihydropyridine-2-carboxylic acid 2-phenylethylamine salt.

$^1$H NMR (DMSO-$D_6$) δ(ppm): 7.8 (br, 2H), 7.51 (m, 2H), 7.3 (m, 13H), 5.98 (s, 1H), 4.94 (s, 2H), 4.03 (m, 2H), 3.13 (m, 2H), 3.05 (m, 2H), 2.88 (m, 2H), 2.23 (s, 3H); MS (m/z): 364 ($C_{22}H_{22}NO_4^+$).

3-Benzyloxy-6-methyl-4-oxo-1-(3-phenylpropyl)-1,4-dihydropyridine-2-carboxylic acid 3-phenylpropylamine salt.

$^1$H NMR (DMSO-$D_6$) δ(ppm): 8.1 (br, 2H), 7.48 (m, 2H), 7.3 (m, 13H), 5.99 (s, 1H), 4.91 (s, 2H), 3.87 (t, J=6.0 Hz, 2H), 2.76 (t, J=5.6 Hz, 2H), 2.60 (m, 4H), 2.17 (s, 3H), 2.07 (m, 2H), 1.85 (m, 2H); MS (m/z): 378 ($C_{23}H_{24}NO_4^+$).

Example 3

Preparation of 3-benzyloxy-1-cyclopropyl-6-methyl-4-oxo-1,4-dihydro-pyridine-2-carboxylic acid methylamide Procedure I:

To a cold suspension (ice-salt bath, internal temp.=4° C.) of 3-benzyloxy-1-cyclopropyl-6-methyl-4-oxo-1,4-dihydropyridine-2-carboxylic acid (150.49 g, 0.50 mol), dichloromethane (750 mL) and dimethylformamide (3.9 mL, 0.05 mol) in a 3N-RBF fitted with a mechanical stirrer was added oxalyl chloride (58.0 mL, 0.66 mol) drop wise over a period of 1 h. The internal temperature was kept at below 10° C. during the addition. After addition of about 30 mL of oxalyl chloride, a dark red solution resulted. The reaction was monitored by thin layer chromatography (TLC, eluent: $CH_2Cl_2$/MeOH, 9/1 ratio). The complete consumption of starting material was observed within 15 min after the addition of oxalyl chloride.

In another 5 L 3N-RBF fitted with a mechanical stirrer was placed dichloromethane (1250 mL), triethylamine (180.0 mL, 1.291 mol) and a solution of 2M methylamine in tetrahydrofuran (325 mL, 0.65 mol). The mixture was cooled in an ice-salt bath and the internal temperature was 4° C. The acid chloride generated in situ above was transferred to an addition funnel, and slowly added to the amine solution over a period of 2.5 h. An exothermic reaction was noticed, but the internal temperature was kept at below 8° C. After 10 min, monitoring of the reaction by TLC ($CH_2Cl_2$/MeOH, 9/1 ratio, v/v) indicated complete consumption of acid chloride, and formation of 3-benzyloxy-1-cyclopropyl-6-methyl-4-oxo-1,4-dihydropyridine-2-carboxylic acid methylamide. The reaction mixture was quenched with brine (500 mL), and the mixture was stirred for 5 min. The organic fraction was collected and washed twice more with brine (2×300 mL), dried over sodium sulfate, filtered and concentrated in vacuo to afford a brown solid. The solid was suspended in 600 mL of a mixture of ethanol and ethyl acetate (1/9 ratio, v/v) and the slurry was stirred for 60 h. The solid was collected by suction filtration, washed with ethyl acetate (50 mL), and was then air-dried. Finally, the solid was dried at 40° C. for 12 h under vacuum to constant weight. The title compound was thus obtained as an off-white, slightly brownish solid (141.1 g, 90%).

M.p. 132-135° C.; $^1$H-NMR (CDCl$_3$, 400 MHz) δ 1.05 (m, 4H, cyclopropyl-H), 2.38 (s, 3H, $CH_3$), 2.70 (d, J=1.8 Hz, 3H, $NCH_3$), 3.35 (m, 1H, CH), 5.07 (s, 2H, $CH_2$), 6.14 (s, 1H, CH), 7.15 (br, 1H), 7.35 (m, 5H, ArH); $^{13}$C(CDCl$_3$) δ 9.48, 20.30, 25.86, 34.15, 74.01, 118.16, 127.79, 128.06(2C), 128.22 (2C), 137.35, 142.05, 143.98, 149.91, 162.01, 173.89; MS (m/z): 313 ($M^+$+1).

Procedure II:

Preparation of 3-benzyloxy-1-cyclopropyl-6-methyl-4-oxo-1,4-dihydro-pyridine-2-carboxylic acid methylamide To a cold suspension (ice-salt bath, internal temp.=5° C.) of 3-benzyloxy-1-cyclopropyl-6-methyl-oxo-1,4-dihydro-pyridine-2-carboxylic acid (100 g, 0.33 mol) and dichloromethane (600 mL) in a 3N-RBF fitted with a mechanical stirrer was added Vilsmeier reagent (54 g, 95%, 0.40 mol) in portions over a period of 15 min. The internal temperature was kept at below 10° C. during the addition. At the end of the addition, a dark red solution resulted. The mixture was left stirring for 1.5 hrs. HPLC analysis showed the complete disappearance of starting material (column: Symmetry C18, 5 nm, 3.9×150 mm, Waters; Mobile phase: 0.035% $HClO_4$/$CH_3CN$ (80/20), isocratic run, flow Rate: 1 ml/min; wavelength: 260 nm).

In another 3 L 3N-RBF fitted with a mechanical stirrer, a cold mixture (ice-salt bath, internal temp.=5° C.) of dichloromethane (600 mL), triethylamine (100.45 mL, 0.73 mol) and a solution of 2M methylamine in THF (200.45 mL, 0.40 mol) was prepared. The acid chloride generated in situ above was transferred to an addition funnel, and slowly added to the amine solution over a period of 1.5 h. An exothermic reaction was noticed, but the internal temp. was kept at below 10° C. After 30 min, monitoring of the reaction by HPLC indicated complete consumption of the acid chloride 3-(benzyloxy)-1-cyclopropyl-6-methyl-4-oxo-1,4-dihydropyridine-2-carbonyl chloride, and formation of 3-benzyloxy-1-cyclopropyl-6-methyl-4-oxo-1,4-dihydro-pyridine-2-carboxylic acid methylamide. The reaction mixture was quenched with de-ionized water (300 mL), and the mixture was stirred for 5 min. The organic fraction was collected and washed twice more with 1:1 mixture of sat. sodium bicarbonate de-ionized water (2×200 mL) and again with de-ionized water (1×200 mL), dried over sodium sulfate, filtered and concentrated in vacuo to afford a brown solid. The solid was suspended in 400 mL of a mixture of methanol and ethyl acetate (5/95 ratio, v/v), and the slurry was stirred for 16 h. The solid was collected by suction filtration, washed with ethyl acetate (50 mL), and was then air-dried. Finally, the solid was dried at 40° C. for 12 h under vacuum to constant weight. The title compound was thus obtained as an off-white, slightly brownish solid (77 g, 73.7%). $^1$H-NMR and MS data were similar to those obtained in the Procedure I above.

Procedure II:

Synthesis of 3-benzyloxy-1-cyclopropyl-6-methyl-4-oxo-1,4-dihydro-pyridine-2-carboxylic acid methylamide To a cold suspension (ice-salt bath, internal temp=−5° C.) of 3-benzyloxy-1-cyclopropyl-6-methyl-oxo-1,4-dihydro-pyridine-2-carboxylic acid (30 g, 0.10 mol), $CH_2Cl_2$ (150 mL) and DMF (7.8 mL, 0.10 mol) in a 3N-RBF fitted with a mechanical stirrer was added thionyl chloride (9.5 mL, 0.13 mol) drop wise over a period of 5 minutes. After addition of thionyl chloride, the reaction mixture was still a suspension. The ice-salt bath was removed. The reaction mixture was allowed to warm up to room temperature. Aliquots were removed and quenched with a 2M methylamine solution in THF. The resulting mixture was then analyzed by HPLC. Thus, HPLC monitoring indicated about 96% consumption of starting material after the reaction mixture was stirred at room temperature for 3 h (HPLC, mobile phase: 0.035% $HClO_4$/$CH_3CN$, 80/20, column: symmetry C18 WAT046980, flow rate: 1 ml/min, monitoring wavelength: 260 nm, RT of 3-benzyloxy-1-cyclopropyl-6-methyl-oxo-1,4-dihydro-pyridine-2-carboxylic acid=2.46 min, RT of 3-benzyloxy-1-cyclopropyl-6-methyl-4-oxo-1,4-dihydro-pyridine-2-carboxylic acid methylamide=5.40 min).

In another 1-L 3N-RBF fitted with a mechanical stirrer was placed dichloromethane (240 mL) and triethylamine (36 mL, 0.26 mol) (ice-salt bath, internal temp=−10° C.). 2M methylamine in tetrahydrofuran (73 mL, 0.146 mol) was added to the cold solution. The acid chloride generated in situ above was transferred to an addition funnel, and slowly added to the amine solution over a period of 30 minutes. An exothermic reaction was noticed, but the internal temperature was kept at below −5° C. The reaction was completed after 10 min as indicated by TLC ($CH_2Cl_2$/MeOH, 9/1 ratio, v/v). The reaction mixture was quenched with water (100 mL), and the mixture was stirred for 5 min. The organic fraction was collected and washed twice more with water, followed by washing with diluted NaOH solution (0.05 M, 3×100 mL), dried over sodium sulfate, filtered and concentrated in vacuo to afford a brown solid. The solid was suspended in 150 mL of a mixture of ethanol and ethyl acetate (2/8 ratio, v/v), and the slurry was stirred for 2 h. The solid was collected by suction filtration, washed with ethyl acetate (50 mL), and was then air-dried. The title compound was thus obtained as a light-pink, slightly brownish solid (14 g, 45%). $^1$H-NMR and MS data were similar to those obtained in the Procedure I above.

Example 4

3-(Benzyloxy)-N-(cyclohexylmethyl)-1-cyclopropyl-6-methyl-4-oxo-1,4-dihydropyridine-2-carboxamide

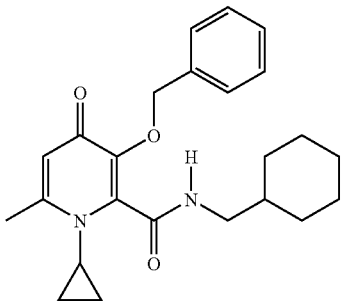

To a cold suspension (ice-salt bath, internal temperature=5° C.) of 3-benzyloxy-1-cyclopropyl-6-methyl-oxo-1,4-dihydro-pyridine-2-carboxylic acid (5.08 g, 17 mmol), $CH_2Cl_2$ and DMF (0.13 mL, 0.17 mmol) in a 3N-RBF was added oxalyl chloride (1.9 mL, 21.8 mmol) drop wise at a rate such that the internal temperature did not exceed 7° C. The resulting mixture was stirred at ice cold temperature for another 30 min, then placed in a dropping funnel and used as described below.

In another 3N-RBF (RBF=round bottom flask), a solution of $Et_3N$ (6 mL, 43 mmol) and cyclohexanemethylamine (3.5 mL, 27 mmol) in dichloromethane was pre-cooled to about 4° C. in an ice-salt bath. The acid chloride generated in situ above was added at such a rate that the internal temperature did not exceed 7° C. The reaction mixture was stirred for another 20 min and the progress of the reaction was monitored by TLC (90/10: dichloromethane/MeOH, v/v). The reaction was quenched with brine. The organic fraction was collected and washed again (2×) with brine, dried over Na₂SO₄, filtered and evaporated to dryness to give a brownish yellow solid. The solid was suspended in ethyl acetate (25 mL) and stirred for 30 min at room temperature. The solid was then collected by suction filtration and dried in a vacuum oven at 40° C. for 30 min. The title compound was thus obtained as a pale yellow solid (5.6 g, 80% yield).

¹H-NMR (CD₃OD,400 MHz) δ 0.90-0.96 (m, 3H), 1.13-1.23 (m, 3H), 1.45-1.54 (m, 1H), 1.64 (br.m, 4H), 1.73-1.76 (br.m, 4H), 2.56 (s, 3H, CH₃), 3.12-3.13 (d, J=6.8 Hz, 2H), 3.36-3.40 (m, 1H, CH), 5.09 (s, 2H), 6.43 (s, 1H), 7.31-7.37 (m, 3H), 7.43-7.45 (m, 2H); MS (m/z): 395 (M⁺+1).

In a similar manner, the following compounds were prepared:

3-(Benzyloxy)-1-cyclopropyl-6-methyl-2-(morpholin-4-ylcarbonyl)pyridin-4(1H)-one

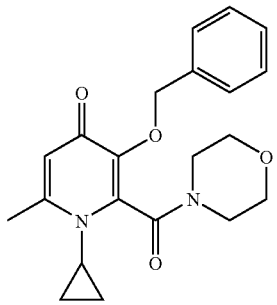

Yield: 69%; ¹H-NMR (CDCl₃,400 MHz) δ 0.87-0.94 (br.m, 1H), 1.09-1.13 (m, 1H), 1.25-1.30 (m, 2H), 2.56 (s, 3H, CH₃), 3.30-3.42 (m, 2H), 3.45-3.69 (m, 6H), 3.84-3.90 (m, 1H, CH), 4.74-4.77 (d, J=10.4 Hz, 1H), 5.54-5.56 (d, J=10.6 Hz, 1H), 6.80 (br.s, 1H, NH), 7.36-7.41 (m, 5H, ArH); MS (m/z): 369 (M⁺+1).

3-(Benzyloxy)-1-cyclopropyl-6-methyl-N-(3-methylbutyl)-4-oxo-1,4-dihydropyridine-2-carboxamide:

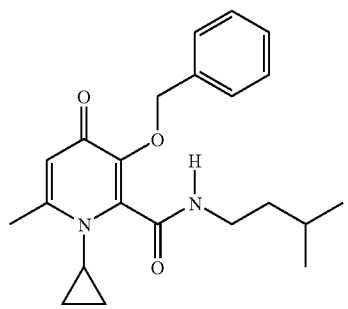

Yield: 62%; ¹H-NMR (CDCl₃,400 MHz) δ 0.86-0.88 (d, J=6.4 Hz, 6H, 2CH₃), 1.04-1.09 (m, 4H), 1.27-1.37 (m, 2H), 1.55-1.60 (m, 1H, CH), 2.37 (s, 3H, CH₃), 3.20-3.25 (m, 2H, CH₂), 3.34-3.37 (m, 1H, CH), 5.09 (s, 2H, CH₂), 6.10 (s, 1H), 7.30-7.38 (m, 5H, ArH), 7.23-2.28 (br.t, 1H, NH).

3-(Benzyloxy)-N-cyclohexyl-1-cyclopropyl-6-methyl-4-oxo-1,4-dihydropyridine-2-carboxamide:

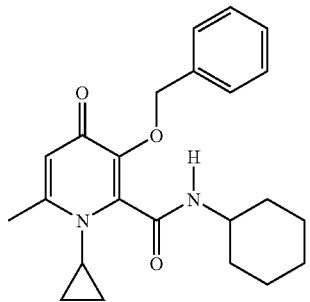

Yield: 63%; ¹H-NMR (CDCl₃,400 MHz) δ 1.15-1.30 (m, 3H), 1.31 (br.m, 1H), 1.34 (br.m, 5H), 1.66-1.70 (m, 1H), 2.78 (s, 3H, CH₃), 3.30-3.34 (m, 1H), 3.42-3.51 (m, 2H), 3.67-3.69 (m, 1H), 3.80-3.83 (m, 1H), 4.82-4.85 (d, J=10.3 Hz, 1H), 5.37-5.40 (d, J=10.5 Hz, 1H), 7.34 (br.m, 5H, ArH), 7.86 (s, 1H).

3-(Benzyloxy)-1-cyclopropyl-N-hexyl-6-methyl-4-oxo-1,4-dihydropyridine-2-carboxamide

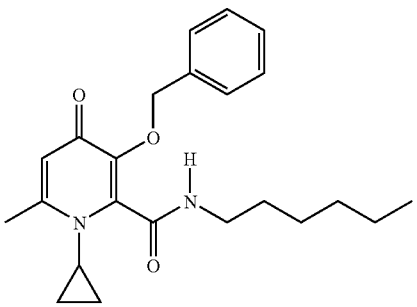

Yield: 47%; ¹H-NMR (CDCl₃,400 MHz) δ 0.89-0.92 (t, J=6.6 Hz, 3H, CH₃), 1.25-1.32 (m, 6H), 1.40-1.47 (m, 4H), 1.64-1.70 (m, 2H, CH₂), 2.54 (s, 3H, CH₃), 3.43-3.48 (m, 2H, CH₂), 3.91-3.93 (m, 1H, CH), 5.10 (s, 2H, CH₂), 7.37-7.46 (m, 6H, ArH and C=CH), 9.24 (br.t, 1H, NH); MS (m/z): 383 (M⁺+1).

3-(Benzyloxy)-1-cyclopropyl-6-methyl-2-[(4-methylpiperazin-1-yl)carbonyl]pyridin-4(1H)-one

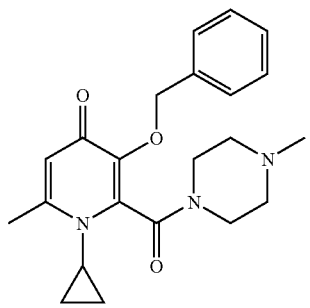

Yield: 65%; ¹H-NMR (CDCl₃,400 MHz) δ 0.85-0.88 (m, 1H), 1.06-1.29 (m, 4H), 1.40-1.45 (br.m, 2H), 1.50-1.58

(br.m, 4H), 2.51 (s, 3H, CH$_3$), 3.12-3.17 (m, 1H), 3.35-3.48 (m, 3H), 3.75-3.78 (m, 1H, CH), 4.76-4.78 (d, J=10.6 Hz, 1H), 5.53-5.56 (d, J=10.7 Hz, 1H), 6.68 (br.s, 1H, NH), 7.30-7.43 (m, 5H, ArH); MS (m/z): 382 (M$^+$+1).

3-(Benzyloxy)-1-cyclopropyl-N,N,6-trimethyl-4-oxo-1,4-dihydropyridine-2-carboxamide

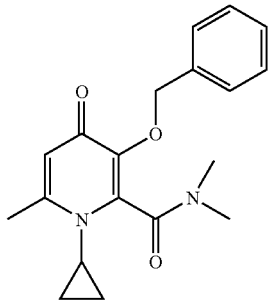

Yield: 43%; $^1$H-NMR (CDCl$_3$, 400 MHz) δ1.16-1.20 (m, 2H), 1.27-1.33 (m, 1H), 1.87-1.95 (m, 1H), 2.78 (s, 3H, CH$_3$), 3.05 (s, 3H, CH$_3$), 3.08 (s, 3H, CH$_3$), 3.62-3.68 (m, 1H, CH), 4.86-4.90 (d, J=10.8 Hz, 1H), 5.33-5.38 (d, J=10.8 Hz, 1H), 7.29-7.33 (m, 5H, ArH), 7.77 (s, 1H, NH); MS (m/z): 327 (M$^+$+1).

Example 5

Preparation of 1-cyclopropyl-3-hydroxy-6-methyl-4-oxo-1,4-dihydro-pyridine-2-carboxylic acid methylamide Procedure I:

Step a. Synthesis of 1-cyclopropyl-3-hydroxy-6-methyl-4-oxo-1,4-dihydro-pyridine-2-carboxylic acid methylamide To a suspension of 3-benzyloxy-1-cyclopropyl-6-methyl-4-oxo-1,4-dihydro-pyridine-2-carboxylic acid methylamide (10.0 g, 0.032 mol) in methanol (40 mL) and water (2.6 mL) at ice-bath temperature, was added conc. HCl (3.9 mL) drop wise. The resulting clear brown solution was stirred at room temperature for ca. 5 min, then nitrogen gas was bubbled into the solution for ca. 5 min. Pd—C (10% wet, 5% w/w, 0.5 g) was added and the reaction vessel was purged with hydrogen twice. The mixture was hydrogenated in a Parr reactor under 50 psi hydrogen pressure at RT, and the progress of the reaction was monitored by HPLC over 3 h. The reaction was over after 3 h.

Excess hydrogen was evacuated and nitrogen gas was bubbled into the solution for about 5 min. The reaction mixture was filtered over pre-treated Celite® (previously washed with a 0.1N standard solution of 1-cyclopropyl-3-hydroxy-6-methyl-4-oxo-1,4-dihydro-pyridine-2-carboxylic acid methylamide in methanol), and the cake was washed with 6×10 mL of methanol. The volume of the filtrate was reduced to about 30 mL under reduced pressure. The residue was cooled in ice and some solid started to precipitate out. A 2N NaOH solution (25 mL) was added until the pH was about 5, and the mixture was stirred for about 10 min. Methyl t-butyl ether (MTBE) (30 mL) was added, and the resulting mixture was stirred at ice-bath temperature for 30 min. The solid was collected by suction filtration, twice thoroughly washed with a mixture of 5 mL of EtOH/MTBE (1/2 ratio). HPLC condition for reaction monitoring: symmetry C18 column (WAT046980), gradient 0.035% HClO$_4$/ACN, min-% ACN: 0-10; 6-10; 7-20 and 15-20, λ at 210, 260 and 285 nm; retention time of 1-cyclopropyl-3-hydroxy-6-methyl-4-oxo-1,4-dihydro-pyridine-2-carboxylic acid methylamide is 2.099 min.

Step b. Purification of 1-cyclopropyl-3-hydroxy-6-methyl-4-oxo-1,4-dihydro-pyridine-2-carboxylic acid methylamide The suspension of crude product obtained as described in Step a in a 1/1 mixture of EtOH/distilled water (14 mL total) was stirred at ice-bath temperature for 1 h. The solid was collected by suction filtration, and washed 2× thoroughly with 5 mL of a 1/1 mixture of pre-cooled EtOH/distilled water. The title compound, a light pinkish solid, was dried to constant weight at 40° C. under vacuum for 16 h. This product gave a negative silver nitrate test, and weighed 5.3 g (74% total yield, steps a and b).

$^1$H-NMR (300 MHz, DMSO-D$_6$) δ(ppm): 0.94-0.99 (m, 4H, 2 c-CH$_2$), 2.39 (s, 3H, CCH$_3$), 2.76 (d, J=4.4 Hz, 3H, NHCH$_3$), 3.28-3.31 (m, 1H, c-CH), 6.08 (s, 1H, C=CH), 8.44 (br. q., 1H, NHCH$_3$); $^{13}$C-NMR (75 MHz, DMSO-D$_6$) δ(ppm): 9.1, 19.9, 25.8, 33.7, 112.3, 130.1, 143.3, 148.7, 161.8, 170.6; MS/MS (+ve ES): MS (m/z) 223 (M$^+$+1), 192.1, 164.2 (M$^+$-CONHCH$_3$, 100%), 150.1, 136.3; Elemental Analysis: Anal. Calcd. for C$_{11}$H$_{14}$N$_2$O$_3$: C, 59.45; H, 6.35; N, 12.60%. Found: C, 59.19; H, 6.07; N, 12.53%;IR (KBr) cm$^{-1}$: 3300 (NH), 1670, 1653, 1495 (C=C).

Procedure II:

To a suspension of 3-benzyloxy-1-cyclopropyl-6-methyl-4-oxo-1,4-dihydro-pyridine-2-carboxylic acid methylamide (10.0 g, 0.032 mol) in methanol (60 mL) and water (10 mL) at ice-bath temperature, was added 37% conc. HCl (2.67 mL, 0.032 mol) drop wise. The resulting clear brown solution was stirred at room temperature for ca. 5 min, then nitrogen gas was bubbled into the solution for ca. 5 min. Pd—C (10% wet, 0.58% w/w, 58 mg) was added and the reaction vessel was purged with hydrogen twice. The mixture was hydrogenated in a Parr reactor under 50 psi hydrogen pressure at RT, and the progress of the reaction was monitored by TLC (9/1 CH$_2$Cl$_2$/MeOH, v/v). The reaction was over after 2.5 h.

Excess hydrogen was evacuated and nitrogen gas was bubbled into the solution for about 5 min. The reaction mixture was filtered over Celite®, and the cake was thoroughly washed (6×) with 10 mL of a mixture of solvent consisting of methanol and distilled water (6/1, v/v). The MeOH was removed under reduced pressure at 35° C. Isopropanol (20 ml) was added to the residue at 35° C., then the mixture was cooled in an ice-bath and solid precipitated out. A 2N NaOH solution (16.5 mL) was added drop wise until the pH was about 5-6, and the mixture was stirred for about 15 min. The pH of the reaction mixture was monitored until it stopped fluctuating between 5 and 6. The solid was then collected by suction filtration, twice thoroughly washed with 7 mL of pre-cooled mixture IPA/distilled water (12/2 ratio).

The title compound, a light pinkish solid (5.985 g, 84.1% yield), was dried to constant weight at 40° C. under vacuum for 6 h. This compound gave a negative silver nitrate test. Spectral data ($^1$H-NMR and MS) were similar as compared to those obtained in procedure 1.

Example 6

N-(Cyclohexylmethyl)-1-cyclopropyl-3-hydroxy-6-methyl-4-oxo-1,4-dihydropyridine-2-carboxamide

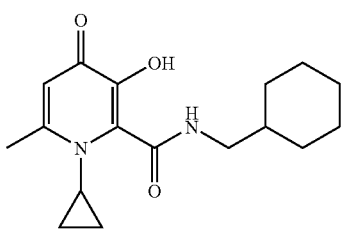

A mixture of 3-(benzyloxy)-N-(cyclohexylmethyl)-1-cyclopropyl-6-methyl-4-oxo-1,4-dihydropyridine-2-carboxamide (2.0 g, 4.8 mmol), Pd/C (10% wet, 0.45 g) in ethanol (150 mL) was hydrogenated in a Parr apparatus at 50 psi of hydrogen pressure for 16 h. The reaction mixture was filtered over a pad of Celite® and the Celite® was thoroughly washed with EtOH (25 mL). Evaporation of the solvent afforded a pale pink solid. The solid was dissolved in hot methanol, then cooled to RT as solid product precipitated out. The solid was collected by suction filtration. The mother liquor was concentrated in vacuo and the residual solid was again dissolved in hot methanol and cooled to RT to precipitate out the product, which was then collected. This process was repeated one more time. The three combined white solid fractions weighed 0.95 g (63% yield).

$^1$H-NMR (CDCl$_3$, 400 MHz) δ 0.84-0.88 (m, 2H), 1.03-1.09 (m, 2H), 1.06-1.31 (m, 5H), 1.65-1.87 (m, 6H), 2.50 (s, 3H, CH$_3$), 3.33-3.36 (m, 2H), 3.51 (s, 1H), 3.58-3.61 (m, 1H, CH), 6.27 (s, 1H), 6.80 (br.t, 1H, NH); MS (m/z): 305 (M$^+$+1).

The following compounds were prepared in a similar fashion:

1-Cyclopropyl-3-hydroxy-6-methyl-N-(3-methylbutyl)-4-oxo-1,4-dihydropyridine-2-carboxamide

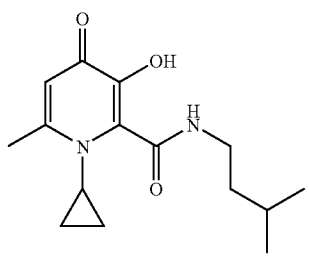

Yield: 88%; $^1$H-NMR (CDCl$_3$, 400 MHz) δ 0.85-0.89 (m, 1H), 0.98-1.00 (d, J=6.4 Hz, 6H, 2CH$_3$), 1.15-1.19 (m, 2H), 1.54-1.60 (m, 2H), 1.72-1.77 (m, 1H, CH), 2.50 (s, 3H, CH$_3$), 3.49-3.53 (m, 2H, CH$_2$), 3.57-3.60 (m, 1H, CH), 3.72 (br.s, 1H), 6.27 (s, 1H), 7.23 (br.t, 1H, NH); MS (m/z): 279 (M$^+$+1).

1-Cyclopropyl-N-hexyl-3-hydroxy-6-methyl-4-oxo-1,4-dihydropyridine-2-carboxamide

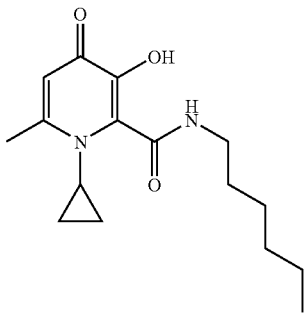

Yield: 87%; $^1$H-NMR (CDCl$_3$, 400 MHz) δ 0.90-0.94 (t, J=6.8 Hz, 3H, CH$_3$), 1.27-1.47 (m, 10H), 1.68-1.73 (m, 2H), 2.70 (s, 3H, CH$_3$), 3.47-3.52 (m, 2H, CH$_2$), 3.85-3.88 (m, 1H, CH), 7.05 (s, 1H, C=CH), 8.30 (br.t, 1H, NH); MS (m/z): 293 (M$^+$+1).

N-Cyclohexyl-1-cyclopropyl-3-hydroxy-6-methyl-4-oxo-1,4-dihydropyridine-2-carboxamide

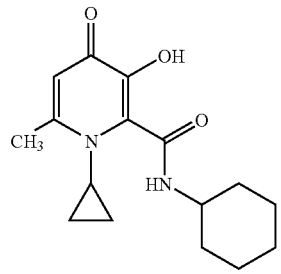

Yield: 91%; $^1$H-NMR (CDCl$_3$, 400 MHz) δ 0.98-1.05 (m, 1H), 1.21-1.38 (m, 3H), 1.60-1.80 (br.m, 7H), 2.71 (s, 3H, CH$_3$), 3.32-3.37 (m, 1H), 3.46-3.50 (m, 1H), 3.55-3.64 (m, 2H), 3.92-3.99 (m, 1H), 6.88 (s, 1H, C=CH); MS (m/z): 277 (M$^+$+1).

1-Cyclopropyl-3-hydroxy-N,N,6-trimethyl-4-oxo-1,4-dihydropyridine-2-carboxamide

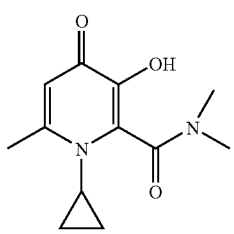

Yield: 97%; $^1$H-NMR (CD$_3$OD, 300 MHz) δ 0.98-1.10 (m, 1H), 1.15-1.43 (m, 3H), 2.76 (s, 3H, CH$_3$), 3.07 (s, 3H, CH$_3$), 3.16 (s, 3H, CH$_3$), 3.70-3.76 (m, 1H, CH), 7.10 (s, 1H, C=CH);

$^{13}$C-NMR (CD$_3$OD, 75 MHz) δ 9.5, 10.9, 21.3, 35.0, 38.1, 38.8, 114.4, 138.8, 142.9, 154.7, 162.5, 162.8; MS (m/z): 237 (M$^+$+1).

1-Cyclopropyl-3-hydroxy-6-methyl-2-[(4-methylpip-erazin-1-yl)carbonyl]pyridin-4(1H)-one

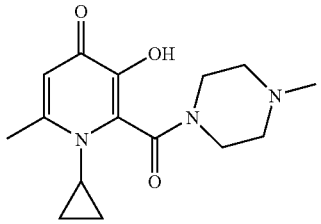

Yield: 96%; $^1$H-NMR (CD$_3$OD,300 MHz) δ 0.89-1.00 (m, 1H), 1.06-1.29 (m, 3H), 1.52-1.85 (br.m, 8H), 2.56 (s, 3H, CH$_3$), 3.40-3.60 (m, 3H), 3.88-3.98 (m, 1H, CH), 6.48 (s, 1H, C=CH);
$^{13}$C-NMR (CD$_3$OD,75 MHz) δ10.0, 11.0, 21.0, 25.4, 26.4, 27.0, 36.5, 43.8, 49.2, 114.7, 132.9, 144.5, 152.8, 162.4, 170.2.

N,1-Dicyclopropyl-3-hydroxy-6-methyl-4-oxo-1,4-dihydropyridine-2-carboxamide

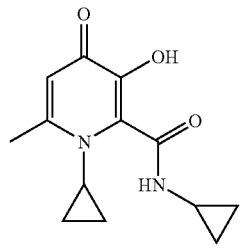

$^1$H-NMR (CDCl$_3$,400 MHz) δ 0.68-0.70 (m, 2H), 0.85-0.95 (m, 4H), 1.15-1.26 (m, 2H), 2.70 (s, 3H, CH$_3$), 2.91-2.98 (m, 1H), 3.50-3.61 (m, 1H), 6.26 (s, 1H, C=CH), 7.10 (br.s, 1H, NH); MS (m/z): 249 (M$^+$+1).

1-Cyclopropyl-3-hydroxy-6-methyl-2-(morpholin-4-ylcarbonyl)pyridin-4(1H)-one

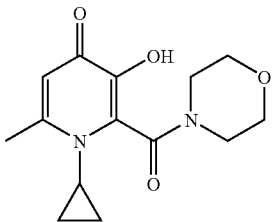

Yield: 43%; $^1$H-NMR (CD$_3$OD,300 MHz) δ 1.00-1.10 (m, 1H), 1.20-1.45 (m, 3H), 2.73 (s, 3H, CH$_3$), 3.45-3.53 (m, 2H), 3.62-3.86 (m, 6H), 3.90-4.00 (m, 1H), 7.02 (s, 1H, C=CH); $^{13}$C-NMR (CD$_3$OD,75 MHz) δ 10.3, 11.1, 21.3, 38.6, 43.6, 48.3, 67.4, 67.7, 114.5, 137.2, 143.3, 154.7, 161.2, 163.7; MS (m/z): 279 (M$^+$+1).

When compared to known processes, the present invention introduces a number of advantages. Significantly, the new process affords 3-benzyloxy-1-cyclopropyl-6-methyl-4-oxo-1,4-dihydro-pyridine-2-carboxylic acid methylamide or 1-alkyl-3-benzyloxy-6-methyl-4-oxo-1,4-dihydro-pyridine-2-carboxylic acid methylamide in considerably higher yields than existing processes. It is a general and efficient process for the preparation of 1-alkyl-3-benzyloxy-6-methyl-4-oxo-1,4-dihydro-pyridine-2-carboxylic acid alkylamide, 3-benzyloxy-1-cycloalkyl-6-methyl-4-oxo-1,4-dihydro-pyridine-2-carboxylic acid alkylamide and 1-alkyl-3-benzyloxy-6-methyl-4-oxo-1,4-dihydro-pyridine-2-carboxylic acid cycloalkylamide. This is in contrast to that described in the existing literature processes (approaches I to III), which are not amenable to large scale synthesis of 3-benzyloxy-1-cyclopropyl-6-methyl-4-oxo-1,4-dihydro-pyridine-2-carboxylic acid methylamide. Specifically, the present process is particularly amenable to industrial scale production as 3-hydroxy-6-methyl-4(1H)-pyran-2-yl-2-carboxy-(N-methyl)-amide (3) is no longer needed as a key intermediate. The key intermediate 3-benzyloxy-(1-cycloalkyl or 1-alkyl)-6-methyl-4-oxo-1,4-dihydro-pyridine-2-carboxylic acid can be made easily in higher yield and purity from cycloalkylamine or alkylamine in water. Further, the compound can be isolated in high purity from simple crystallization without the need for chromatographic separation.

Advantageously, the use of intermediate 3-(2-carbonyl-3-benzyloxy-6-methyl-4(1H)-pyran-2-yl)-1,3-thiazolidine-2-thione is eliminated. In addition, the process does not use 2-mercaptothiazoline which requires removal as chemical waste in the later step and avoids the use of reagent dicyclohexylcarbodiimide and the subsequent generation of dicyclohexylurea waste, both of which are known skin irritants.

The invention claimed is:
1. A process for the manufacture of a compound of formula I:

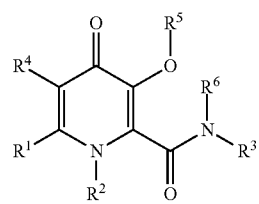

comprising:
reacting one or more acid chloride formation reagents with a compound of formula III:

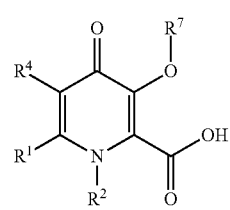

thereby forming an intermediate; and
reacting the intermediate with an amine R$^3$R$^6$NH to give the compound of formula I,
wherein:
R$^1$ is selected from the group consisting of hydrogen and C$_1$-C$_6$ alkyl;
R$^2$ is selected from the group consisting of C$_1$-C$_6$ alkyl and C$_3$-C$_6$ cycloalkyl;
R$^3$ is selected from the group consisting of C$_1$-C$_6$ alkyl, C$_3$-C$_6$ cycloalkyl, hydrogen and C$_1$-C$_6$ alkyl-[C$_3$-C$_6$ cycloalkyl] with the attachment at the alkyl group;
R$^4$ is selected from the group consisting of hydrogen and C$_1$-C$_6$ alkyl;
R$^5$ is selected from the group consisting of hydrogen, benzyl, a substituted benzyl group, and an alcohol protective group removable using acid/base hydrolysis or catalytic hydrogenation, wherein the substituted benzyl is substituted with 1 to 3 substituents selected from halo, $C_1$-$C_4$ alkyl and $C_1$-$C_4$ alkoxy;

$R^6$ is selected from the group consisting of $C_1$-$C_6$ alkyl, $C_3$-$C_6$ cycloalkyl and hydrogen; or $R^3R^6N$ when taken together form an unsubstituted or substituted heterocyclic ring selected from the group consisting of piperidinyl, morpholinyl, pyrrolidinyl and piperazinyl, wherein the substituted heterocyclic ring is substituted with one to three $C_1$-$C_6$ alkyl groups;

$R^7$ is selected from the group consisting of benzyl, a substituted benzyl, and an alcohol protective group removable using acid/base hydrolysis or catalytic hydrogenation, wherein the substituted benzyl is substituted with 1 to 3 substituents selected from the group consisting of halo, $C_1$-$C_4$ alkyl and $C_1$-$C_4$ alkoxy; and provided that, when $R^5$ is hydrogen, $R^7$ is an alcohol protective group removable by acid/base hydrolysis or catalytic hydrogenation and $R^7$ is removed by acid/base hydrolysis or catalytic hydrogenation after reacting the intermediate with the amine.

2. The process according to claim 1 wherein $R^1$ is methyl, $R^2$ is cyclopropyl, $R^4$ is hydrogen, $R^5$ is benzyl and $R^7$ is benzyl.

3. The process according to claim 1 wherein $R^3$ is methyl and $R^6$ is hydrogen and said acid chloride forming reagent is oxalyl chloride and dimethylformamide.

4. The process according to claim 1 wherein $R^3$ is methyl, $R^6$ is hydrogen and said acid chloride forming reagent is dimethylchloromethylene-ammonium chloride.

5. The process according to claim 1 wherein $R^3$ is methyl and $R^6$ is hydrogen and said acid chloride forming reagent is thionyl chloride and dimethylformamide.

6. The process according to claim 1 wherein $R^5$ is benzyl and $R^7$ is benzyl.

7. The process according to claim 1 wherein said one or more acid chloride formation reagents are selected from oxalyl chloride and dimethylformamide; dimethylchloromethylene-ammonium chloride; and thionyl chloride and dimethylformamide.

8. The process according to claim 6 wherein $R^1$ is methyl, $R^4$ is hydrogen, $R^2$ is cyclopropyl, $R^3$ is methyl and $R^6$ is hydrogen.

9. A process for the manufacture of a compound of formula I:

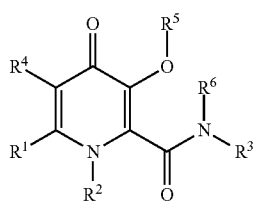

the process comprising:

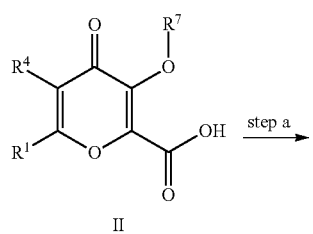

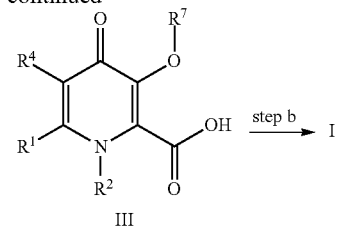

wherein step a comprising:
reacting a first amine $R^2NH_2$ with a compound of formula II in an aqueous solution selected from the group consisting of aqueous sodium hydroxide solution, aqueous potassium hydroxide solution and mixtures thereof, to give a compound of formula III; and step b comprising:
reacting the compound of formula III with an acid chloride formation reagent thereby forming an intermediate; and reacting the intermediate with a second amine $R^3R^6NH$, to give the compound of formula I, wherein:

$R^1$ is selected from the group consisting of hydrogen and $C_1$-$C_6$ alkyl;

$R^2$ is selected from the group consisting of $C_1$-$C_6$ alkyl and $C_3$-$C_6$ cycloalkyl;

$R^3$ is selected from the group consisting of $C_1$-$C_6$ alkyl, $C_3$-$C_6$ cycloalkyl, hydrogen and $C_1$-$C_6$ $_{alkyl\text{-}[C3}$-$C_6$ cycloalkyl] with the attachment at the alkyl group;

$R^4$ is selected from the group consisting of hydrogen and $C_1$-$C_6$ alkyl;

$R^5$ is selected from the group consisting of hydrogen, benzyl, a substituted benzyl, and an alcohol protective group removable using acid/base hydrolysis or catalytic hydrogenation, wherein the substituted benzyl is substituted with 1 to 3 substituents selected from the group consisting of halo, $C_1$-$C_4$ alkyl and $C_1$-$C_4$ alkoxy;

$R^6$ is selected from the group consisting of $C_1$-$C_6$ alkyl, $C_3$-$C_6$ cycloalkyl and hydrogen; or $R^3R^6N$ when taken together, form an unsubstituted or substituted heterocyclic ring selected from the group consisting of piperidinyl, morpholinyl, pyrrolidinyl or piperazinyl, wherein the substituted heterocyclic ring is substituted with one to three $C_1$-$C_6$ alkyl;

$R^7$ is selected from the group consisting of benzyl, substituted benzyl, and an alcohol protective group removable using acid/base hydrolysis or catalytic hydrogenation, wherein the substituted benzyl is substituted with 1 to 3 substituents selected from the group consisting of halo, $C_1$-$C_4$ alkyl and $C_1$-$C_4$ alkoxy; and provided that, when $R^5$ is hydrogen, $R^7$ is an alcohol protective group removable by acid/base hydrolysis or catalytic hydrogenation and $R^7$ is removed by acid/base hydrolysis or catalytic hydrogenation after reaction of the intermediate with the second amine.

10. The process according to claim 9 wherein $R^1$ is methyl, $R^2$ is cyclopropyl, $R^4$ is hydrogen, $R^5$ is benzyl and $R^7$ is benzyl.

11. The process according to claim 9 wherein $R^3$ is methyl and $R^6$ is hydrogen and said acid chloride forming reagent is oxalyl chloride and dimethylformamide.

12. The process according to claim 9 wherein $R^3$ is methyl, $R^6$ is hydrogen and said acid chloride forming reagent is dimethylchloromethylene-ammonium chloride.

13. The process according to claim 9 wherein $R^3$ is methyl and $R^6$ is hydrogen and said acid chloride forming reagent is thionyl chloride and dimethylformamide.

14. The process according to claim 9 wherein $R^5$ is benzyl and $R^7$ is benzyl.

15. The process according to claim 9 wherein said one or more acid chloride formation reagents are selected from oxalyl chloride and dimethylformamide; dimethylchloromethylene-ammonium chloride; and thionyl chloride and dimethylformamide.

16. The process according to claim 14 wherein $R^1$ is methyl, $R^4$ is hydrogen, $R^2$ is cyclopropyl, $R^3$ is methyl and $R^6$ is hydrogen.

17. A process for the manufacture of a compound of formula IA

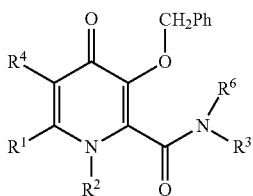

comprising:
reacting one or more acid chloride formation reagents with a compound of formula IIIA

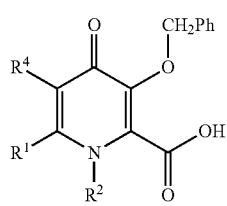

thereby forming an intermediate; and
reacting the intermediate with an amine $R^3R^6NH$, thereby forming the compound of formula IA;

wherein:
$R^1$ is selected from the group consisting of hydrogen and $C_1$-$C_6$ alkyl;

$R^2$ is selected from the group consisting of $C_1$-$C_6$ alkyl and $C_3$-$C_6$ cycloalkyl;

$R^3$ is selected from the group consisting of $C_1$-$C_6$ alkyl, $C_3$-$C_6$ cycloalkyl, hydrogen and $C_1$-$C_6$ alkyl-[$C_3$-$C_6$ cycloalkyl] with the attachment at the alkyl group;

$R^4$ is selected from the group consisting of hydrogen and $C_1$-$C_6$ alkyl; and $R^6$ is selected from the group consisting of $C_1$-$C_6$ alkyl, $C_3$-$C_6$ cycloalkyl and hydrogen; or $R^3R^6N$ when taken together foim an unsubstituted or substituted heterocyclic ring selected from the group consisting of piperidinyl, morpholinyl, pyrrolidinyl and piperazinyl, wherein the substituted heterocyclic ring is substituted with one to three $C_1$-$C_6$ alkyl groups.

18. The process according to claim 17 wherein $R^1$ is methyl, $R^2$ is cyclopropyl, and $R^4$ is hydrogen.

19. The process according to claim 17 wherein $R^3$ is methyl and $R^6$ is hydrogen and said acid chloride forming reagent is oxalyl chloride and dimethylformamide.

20. The process according to claim 17 wherein $R^3$ is methyl, $R^6$ is hydrogen and said acid chloride forming reagent is dimethylchloromethylene-ammonium chloride.

21. The process according to claim 17 wherein $R^3$ is methyl and $R^6$ is hydrogen and said acid chloride forming reagent is thionyl chloride and dimethylformamide.

22. The process according to claim 17 wherein said one or more acid chloride formation reagents are selected from oxalyl chloride and dimethylformamide; dimethylchloromethylene-ammonium chloride; and thionyl chloride and dimethylformamide.

* * * * *